United States Patent
Pustjens et al.

(10) Patent No.: US 12,115,512 B2
(45) Date of Patent: Oct. 15, 2024

(54) CHEMICAL REACTOR WITH INTERNAL STATIC MIXERS

(71) Applicant: STAMICARBON B.V., Sittard (NL)

(72) Inventors: Ronny Albert Mathijs Pustjens, Sittard (NL); Johan Albert Arno Van Den Tillaart, Melick (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 18/257,475

(22) PCT Filed: Apr. 28, 2022

(86) PCT No.: PCT/NL2022/050230
§ 371 (c)(1),
(2) Date: Jun. 14, 2023

(87) PCT Pub. No.: WO2022/231428
PCT Pub. Date: Nov. 3, 2022

(65) Prior Publication Data
US 2024/0082808 A1  Mar. 14, 2024

(30) Foreign Application Priority Data

Apr. 28, 2021  (EP) .................................... 21170983

(51) Int. Cl.
*B01J 19/24* (2006.01)
*B01J 19/00* (2006.01)
*C07C 273/04* (2006.01)

(52) U.S. Cl.
CPC ........... *B01J 19/24* (2013.01); *B01J 19/0066* (2013.01); *B01J 19/249* (2013.01); *C07C 273/04* (2013.01); *B01J 2219/2458* (2013.01)

(58) Field of Classification Search
CPC .... B01J 19/006; B01J 19/0066; B01J 19/249; B01J 2219/2422; B01J 2219/2458;
(Continued)

(56) References Cited

U.S. PATENT DOCUMENTS 5,750,080 A * 5/1998 Pagani ................ B01J 19/0053
422/607
5,888,460 A  3/1999 Zardi et al.
(Continued)

FOREIGN PATENT DOCUMENTS

EP  2197837 B1  6/2010
EP  2797882 A1  11/2014
(Continued)

OTHER PUBLICATIONS

Ullmann's Encyclopaedia, chapter Urea, 2010.
(Continued)

*Primary Examiner* — Lessanework Seifu
(74) *Attorney, Agent, or Firm* — Leason Ellis LLP (57) ABSTRACT

Embodiments of the disclosure pertain to a chemical reactor comprising a mixing zone comprising first static mixer and a second static mixer both arranged in shell of the reactor, wherein the second static mixer is positioned further from said first inlet than said first static mixer, wherein the second static mixer is adapted for more intimate mixing of fluids in the reaction mixture than the first static mixer.

23 Claims, 3 Drawing Sheets

(58) Field of Classification Search
CPC ..... B01J 2219/0077; B01J 2219/00777; C07C 273/04
See application file for complete search history.

(56) References Cited

U.S. PATENT DOCUMENTS

| | | | |
|---|---|---|---|
| 6,123,323 A * | 9/2000 | Yoneda | B01D 53/18 422/220 |
| 6,165,315 A | 12/2000 | Jonckers et al. | |
| 2007/0070807 A1 | 3/2007 | Bracht et al. | |
| 2011/0174407 A1 | 7/2011 | Lundberg et al. | |
| 2014/0171686 A1 | 6/2014 | Avagliano et al. | |
| 2015/0119603 A1 | 4/2015 | Van Den Tillaart et al. | |
| 2015/0322000 A1 | 11/2015 | Buitink et al. | |
| 2018/0280921 A1 | 10/2018 | Avagliano et al. | |
| 2020/0385339 A1 | 12/2020 | Patil et al. | |
| 2021/0071287 A1 | 3/2021 | Paci et al. | |

FOREIGN PATENT DOCUMENTS

| | | | |
|---|---|---|---|
| EP | 2596859 B1 | 10/2016 | |
| WO | 9531278 A1 | 11/1995 | |
| WO | 9950235 A1 | 10/1999 | |
| WO | 2011134648 A1 | 11/2011 | |
| WO | 2021006729 A1 | 1/2021 | |

OTHER PUBLICATIONS

First Chinese Office Action in CN Application No. 202280031582.2, mailed Jan. 30, 2024, an English Translation attached hereto (15 pages).

* cited by examiner

CHEMICAL REACTOR WITH INTERNAL STATIC MIXERS

CROSS-REFERENCE TO RELATED PATENT APPLICATIONS

This application is a U.S. National Stage Application under 35 U.S.C. § 371 of International Patent Application No. PCT/NL2022/050230 filed Apr. 28, 2022, which claims the benefit of priority of European Patent Application No. 21170983.7 filed Apr. 28, 2021, both of which are incorporated by reference in their entireties. The international application was published on Nov. 3, 2022, and received publication no. WO/2022/231428 A1.

FIELD

The invention pertains to a chemical reactor, for example a urea synthesis reactor, as well as to a urea production plant comprising the urea synthesis reactor and a urea production process wherein the urea synthesis reactor is used.

INTRODUCTION

The chemical reactor according to the invention comprises a shell for holding fluids, a first inlet for a first fluid stream and a separate second inlet for a second fluid stream. The first and second inlet are both arranged in a first section of the shell, wherein the first section is for instance a bottom section. The first inlet and second inlet are for instance arranged in parallel in said first section.

In many chemical processes there is a need for mixing of the first and second fluid in said first section of the chemical reactor. For instance, the first fluid comprises a first reactant, and the second fluid comprises a second reactant and the first and second reactant are to be reacted with each other in the chemical reactor. The first and second reactant are different from each other. The first and second fluid are different from each other and have at least a different chemical composition.

Examples of chemical reactors having a first and a second inlet include urea synthesis reactors used in certain types of urea production processes.

The chemical reactor according to the invention is for instance a urea synthesis reactor of a urea plant for the synthesis of urea from an $NH_3$ feed and a $CO_2$ feed. In an example urea production process according to an aspect of the invention, the urea formation reaction involves the exothermic reaction of $NH_3$ and $CO_2$ into ammonium carbamate (carbamate) and the endothermic dehydration of carbamate into water and urea in a high pressure synthesis section comprising a reaction zone. The carbamate condensation reaction is exothermic and occurs fast at a pressure above 100 bar and a temperature above 150° C. Ammonium carbamate is extremely corrosive at the operating temperature of the reactor of typically above 140° C. Moreover the mixing of $CO_2$ and $NH_3$ under formation of carbamate is strongly exothermic and may lead to hot spots in the bottom section of the urea synthesis reactor and subsequent corrosion of the reactor and internal reactor parts.

The overall reaction yields as reactor effluent a urea synthesis stream comprising a liquid phase comprising at least urea, water, carbamate and ammonia. The reactor effluent is withdrawn at an outlet of the reactor in urea production processes according to the invention.

In an example urea production process according to the invention, the urea synthesis stream is purified by dissociation of carbamate into $NH_3$ and $CO_2$ and by gas/liquid separation to give a urea solution and a gas stream. The urea purification is carried out in one or more downstream processing units comprised for instance in the high pressure synthesis section of the urea plant (e.g. in a high pressure stripper) and/or for instance in a recovery section operated at medium or low pressure of the urea plant according to the invention.

In embodiments wherein the chemical reactor of the invention is a urea synthesis reactor, the urea synthesis reactor can be used with numerous types of high pressure synthesis sections and recovery sections of urea production plants.

An example urea production process using a high pressure stripper is illustrated in FIG. 25 of Ullmann's Encyclopaedia, chapter Urea, 2010 showing a process scheme of the 'Snamprogetti self-stripping process'. In this process scheme, the reactor receives at the bottom a $CO_2$ feed stream and a separate feed stream essentially consisting of feed $NH_3$ and carbamate recycle solution. These feed streams are illustrated as two separate flow lines into the reactor.

US 2018/0280921A1 to Saipem SpA shows in FIG. 1 an example urea reactor with two feeding pipes at the bottom for $NH_3$/carbamate feed and $CO_2$ feed respectively. US '921 mentions that this type of urea reactor has certain drawbacks; most importantly the lack of uniform distribution of reagents over the entire cross-section of the reactor. US '921 proposes (FIG. 2, FIG. 3) the use of an annular perforated tubular distributor 15 for the $CO_2$ feed and an L-shaped tubular distributor 16 for $NH_3$ feed with a downward perforated tubular end 26.

The above-mentioned US 2018/0280921A1 states that $CO_2$, which due to its density constitutes the light phase in the urea synthesis reaction, tends to form a vertical column above the related inlet, in this way strongly limiting reaction kinetics, which would instead be favoured by the uniform distribution of $CO_2$ in small bubbles over the entire cross-section of the reactor, and that even the distribution of the (liquid) heavy phase, formed of ammonia and ammonium carbamate, is not entirely satisfactory in existing urea reactors.

EP2596859B1 describes a gas-liquid reactor that can be used as a urea synthesis reactor and that comprises a vertical body with inlet pipes for reactants and outlet pipes for reaction products, a mixer with a coaxial tube and a vortex chamber located in the lower part of the body, wherein an axial outlet pipe of the mixer is fitted with a diffuser illustrated as a diverging tube part.

A urea synthesis reactor provided with perforated reactor trays is described e.g. in U.S. Pat. No. 6,165,315 to Jonckers et al.

Reference can also be made to an example total recycle process without a high pressure stripper as shown in FIG. 12 of Ullmann's Urea 2010. The $CO_2$ feed is compressed, the $NH_3$ feed is separately supplied, the two feeds are combined in a unit and the combined stream is supplied from this unit to the inlet at the bottom of the reactor. Carbamate recycle solution is additionally combined in said unit into the combined stream. The reactor has only one feed inlet.

There remains a desire for a chemical reactor comprising a first inlet for a first fluid stream and a second inlet for a second fluid stream, wherein the configuration of the reactor provides for good mixing of the first and second fluid inside the chemical reactor.

A particular objective for certain embodiments described herein is to provide such a chemical reactor, wherein the reactor is a vertical reactor, wherein the first and second inlet are both arranged in the bottom section of the reactor and the reactor comprises an outlet for reactor effluent withdrawn from a top section of the reactor. The reactor comprises a mixing zone in said bottom section providing for good mixing of the fluids from said first and second inlet.

A further particular objective for certain embodiments described herein is providing such a chemical reactor comprising a mixing zone comprising internal mixing elements, wherein the internal mixing elements have good corrosion resistance and provide for good mixing of the fluids from said inlets.

A further particular objective for certain embodiments described herein is providing a urea synthesis reactor having at least two inlets at the bottom and comprising a mixing zone providing for good mixing of the fluids from said inlets. The internal reactor parts of the urea synthesis reactor are desirably highly corrosion resistant.

SUMMARY

The invention pertains in a first aspect to a chemical reactor comprising a shell for holding a reaction mixture, a first section and a second section in said shell, a first inlet for a first fluid stream and a second inlet for a second fluid stream, wherein both inlets are arranged in said first section, the reactor further comprising an outlet for reactor effluent withdrawn from said second section, and a mixing zone in said first section of the reactor adapted for mixing said first and second fluid stream, wherein the mixing zone comprises a first static mixer and a second static mixer both arranged in said shell, wherein the second static mixer is positioned further from said first inlet than said first static mixer, wherein the second static mixer is preferably adapted for more intimate mixing of fluids in the reaction mixture than the first static mixer. The chemical reactor is for instance a urea synthesis reactor. Preferences and features described hereinbefore and hereinafter in connection with the chemical reactor apply also for the urea synthesis reactor.

In a further aspect the invention pertains to a urea production plant comprising a high pressure synthesis section comprising an inlet for $NH_3$ feed, an inlet for $CO_2$ feed, and a chemical reactor according to the invention comprising said first and second static mixer as urea synthesis reactor, wherein said outlet for urea synthesis stream is connected to a carbamate dissociation section comprising a heat exchanger and/or an expansion valve, preferably wherein the carbamate dissociation section comprises a vertical falling-film shell-and-tube heat exchanger configured for receiving urea solution at the upper inlet of the tubes.

In a further aspect the invention pertains to a urea production process comprising reacting a $NH_3$-containing feed stream and a $CO_2$-containing feed stream to form ammonium carbamate and dehydration of ammonium carbamate to urea and water under urea-forming conditions in a chemical reactor according to to the invention comprising said first and second static mixer as urea synthesis reactor.

Preferences and features described for the urea synthesis reactor apply also for the reactor used in the urea production plant and for the process according to the invention.

The invention also pertains to a mixing process carried out in a chemical reactor according to the invention.

Any embodiments illustrated in the figures are examples only and do not limit the invention.

DETAILED DESCRIPTION

Embodiments of the present invention are based on the judicious insight that arranging a mixing zone comprising a first and a second static mixer inside the shell of the reactor, provides for the efficient and thorough mixing of the first fluid stream from the first inlet with the second fluid stream from the second inlet.

The first and second mixer provide for a simple design, with good mechanical strength and corrosion resistance and efficient mixing of the fluids from the first and second inlet.

The chemical reactor according to the invention comprises a shell for holding a reaction mixture. The chemical reactor can also be identified as a mixing unit, for instance if the unit is used in non-reactive processes of mixing fluids. The shell comprises for instance a pressure-resistant wall configured for withstanding pressures of e.g. above 100 bar inside the shell. The reactor can also be described as comprising a vessel comprising a wall and a vessel space for holding the reaction mixture. The wall is for instance configured for withstanding internal vessel pressures of above 100 bar.

The reactor comprises e.g. a cylindrical shell having in some embodiments a diameter of e.g. at least 1.0 m, for instance 1.0-4.5 m, and/or a length of for instance at least 10 m or for instance at least 20 m, e.g. up to 40 m. In other embodiments the reactor can have different dimensions. The mentioned dimensions are preferred in embodiments wherein the chemical reactor is a urea synthesis reactor. The reactor is arranged preferably vertically with the length in the vertical direction.

In some embodiments, the reactor does not comprise a tube bundle. In some embodiments, the reactor comprises a tube bundle, for instance for cooling fluid in the tubes. The bundle for example extends over 10-50% of the length of the reactor. For example, the fluid on the shell side is cooled, and the heat is transferred from the shell side to cooling water in the tube side to produce steam in the tubes.

The reactor may comprise for instance trays. The reactor may also comprise one or more baffles. In some embodiments, the first section (e.g. bottom section) does not contain trays between the second static mixer and the first and second inlet.

The reactor comprises a first section and a second section in said shell, wherein the first and second section are arranged preferably at opposed ends of said shell. For instance the reactor is a vertical reactor and the first section is a bottom section and the second section is a top section, or the first section is a top section and the second section is a bottom section. In a particular embodiment, the reactor is a urea synthesis reactor, wherein the urea synthesis reactor is a vertical reactor and the first section is the bottom section of the reactor and the reactor is adapted for withdrawing reactor effluent from the top of the reactor. The first section is provided upstream of the second section. The first section extends e.g. over less than 30% or over up to. 20% or up to. 10% of the length of the reactor, e.g. over 3-10% of the length of the reactor and comprises e.g. the first and second static mixer as well as the first and second inlet. For instance, the first and second static mixer are both located at a distance from the first and second inlet that is less than 30% or less than 20% or up to 10% of the length of the reactor, for example 3-10%, preferably 5-7% of the length or the reactor. For instance the volume of the first section is 3-10%, preferably 5-7% of the volume of the reactor.

The first section comprises a first inlet for a first fluid stream and a second inlet for a second fluid stream. The first and second inlet are separate from each other and are spaced apart from each other. For instance, the first and second inlet are both arranged in the bottom of the shell. The first inlet and the second inlet are both arranged in said first section.

Preferably the first and second section independently, preferably both, extend over the entire cross-section of the reactor perpendicular to the reactor length.

The first and second inlet are connected to different supply lines. The first and second inlet are arranged for supplying the first and second fluid streams separately into the reactor volume.

The first and second inlet preferably independently do not protrude from the shell (vessel wall) into the reactor volume. This may advantageously contribute to improved mixing by avoiding stagnant zones of the reaction mixture that could form around protruding tubes. This may also be advantageous to avoid corrosion in such zones in a urea synthesis reactor.

The reactor optionally comprises one or more further inlets arranged in said first section, wherein the first section is e.g. the bottom section.

The reactor further comprises an outlet for reactor effluent withdrawn from said second section. The outlet is for instance arranged for withdrawing fluid reaction mixture from said second section, e.g. from a top section of the reactor.

The reactor effluent is e.g. withdrawn from said top section, using for example a downcomer or for example an outlet arranged in said top section. The reactor may comprise for instance one or more additional outlets. In some embodiments, the top section of the chemical reactor is configured for gas/liquid separation and the reactor comprises a first outlet for liquid, e.g. urea synthesis solution, and a second outlet for gas. For instance the first outlet for liquid is connected to a downcomer. The outlet for the downcomer is for instance connected to a HP stripper or a recovery section, in case of a urea synthesis reactor.

The reactor comprises a mixing zone in said first section of the reactor. The mixing zone is adapted for mixing said first and second fluid. The mixing zone is for instance adapted for mixing the fluids from the first and second inlet with each other. The mixing zone comprises a first static mixer and a second static mixer. The first and second static mixer are both arranged in said shell. Thereby the first and second static mixer are both arranged inside the reactor, in particular inside the vessel. The first and second static mixer are separate and distinct elements and are spaced apart from each other. Preferably the reactor comprises a space between the first and second static mixer. Preferably this space provides for unobstructed flow of fluid from the first to the second static mixer. The first and second static mixer are for instance both attached to the shell, e.g. using separate connecting elements. The first and second static mixer can for instance be separately disassembled and removed from the reactor for instance via a manhole of the reactor. In some embodiments, the first and second static mixer are attached to each other, and optionally also to the optionally used gas distributor to form a mixing unit. This mixing unit is for instance connected to the shell.

The second static mixer is positioned further from said first inlet than said first static mixer. Thereby the distance between the second static mixer and the first inlet is larger than the distance between the first static mixer and the first inlet. Additionally, preferably, the distance between the second static mixer and the second inlet is larger than the distance between the first static mixer and the second inlet. The second static mixer is arranged downstream of the first static mixer, relative to the flow of the first and second fluid stream. In some embodiments the reactor is a vertical reactor and the inlets are arranged in a bottom section and the second static mixer is arranged above the first static mixer.

The first and second static mixer have a different design.

The second static mixer is preferably adapted for more intimate mixing of fluids that are comprised in the reaction mixture than the first static mixer. The second static mixer is for instance adapted for providing a more homogeneous fluid at the downstream end of the second static mixer than the first static mixer when said mixers receive the same inhomogeneous fluid at the inlet.

The first and second static mixer are particularly each adapted for mixing at least the fluids entering the reactor from the first and second inlet by inducing turbulence. Preferably, the first and second fluid stream can flow from the first and second inlet to the first static mixer essentially unobstructed.

Preferably, the shell is a cylindrical shell. Preferably the shell is a vertical shell. Preferably the shell is a cylindrical high pressure shell which is for instance provided with bottom and top closure elements. The shell is for instance provided with hemi head caps or for instance flat plates at the bottom and/or top.

The shell for instance comprises a carbon steel pressure-bearing wall and a corrosion-resistant inner wall, such as lining or overlay welding. The inner surface, e.g. the lining, is made e.g. of duplex stainless steel, especially in case of a urea synthesis reactor.

The mixing zone of the inventive reactor comprises a first static mixer and a second static mixer both arranged in said shell, in particular both comprised in said first section. Static mixers are also known as 'motionless mixers'.

The second static mixer is spaced apart from the first mixer by a distance in the longitudinal direction of the reactor that is preferably less than 5% of the length of the reactor and/or is e.g. at least 0.10% of the length of the reactor or at least 10 cm. Herein, the longitudinal direction refers to the direction in the length of the reactor. For instance the reactor is a vertical reactor and the longitudinal direction is the vertical direction. In some embodiments, the reactor comprises a cylindrical shell having a length and a diameter and the longitudinal direction is in the length direction of the shell, irrespective of the orientation of the reactor. Preferably, the inlets and outlet(s) of the reactor are at opposed ends of the reactor in the longitudinal direction, and the direction from the inlets to the outlet(s) is the length direction.

The second static mixer is for instance arranged downstream of the first static mixer, relative to the flow direction of the fluids in the reactor.

The second static mixer is preferably adapted for more intimate mixing of fluids in the reaction mixture than the first static mixer.

By arranging two static mixers in this way inside the reactor, the different fluids will mix rapidly and efficiently and in a small volume thereby improving the reactor efficiency. Moreover the heat distribution is improved by the mixing thereby preventing or avoiding corrosion problems especially in urea synthesis reactors.

The preferred increasingly intimate mixing of the first and second static mixer can be expressed for instance by the characteristic mixing parameter ($M_c$):

$$\frac{D}{d} = M_c$$

whereby D is the diameter of the reactor; whereby d is a characteristic diameter of the mixing element. In some preferred embodiments, which do not limit the invention, $M_c$ for the first static mixer is in the range 1 to 50 and $M_c$ for the second static mixer is in the range 50-1000, e.g. 55-1000, and/or preferably at least 2 times larger than the $M_c$ of the first static mixer. The characteristic diameter of the mixing element refers to the characteristic size of the channels of the mixing element. The channels of a mixing element are the channels provided by the mixing element for fluid flow.

Figure 1:
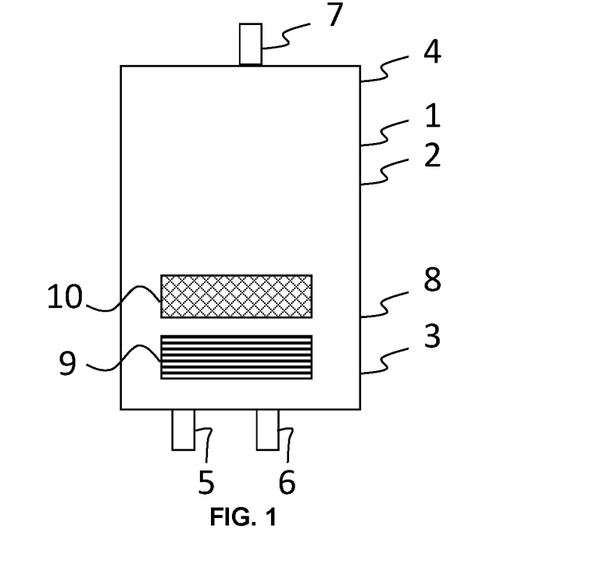
FIG. 1 schematically illustrates an example chemical reactor according to the invention.

FIG. 1 schematically illustrates an example chemical reactor according to the invention. The chemical reactor (1) comprises a vertical shell (2) for holding a reaction mixture, and a first section (3) and a second section (4) in said shell. The second section (4) is arranged downstream of the first section (3). In this example, the first section (3) is a bottom section and the second section (4) is a top section and fluids flow from bottom to top in operation of the reactor. In an alternative embodiment, the reactor can be operated with fluid flow from top to bottom, or optionally as a horizontal reactor.

The rector further comprises a first inlet (5) for a first fluid stream, and a separate second inlet (6) for a distinct second fluid stream. Both inlets are arranged in said bottom section. The reactor further comprises an outlet (7) for a reactor effluent withdrawn from the second section e.g. the upper section. The reactor also comprises a mixing zone (8) in the first section (3) of the reactor. The mixing zone (8) comprises a first static mixer (9) and a second static mixer (10). Both static mixers are arranged inside the shell, i.e. inside the reaction vessel. Both static mixers are arranged in the first section (3). The second static mixer is positioned downstream of the first static mixer. In this example, the second static mixer is positioned above the first static mixer. The first and second static mixer are spaced apart from each other. The second static mixer is adapted for more intimate mixing of fluids in the reaction mixture than the first static mixer.

Generally in the inventive chemical reactor, the first static mixer and the second static mixer preferably each comprises mixing elements and channels, wherein the channels are configured for allowing the reaction mixture to flow through the shell. Preferably the channels comprised in the second static mixer are narrower than the channels comprised in the first static mixer. The channels are at least in part delimited by the mixing elements.

Preferably the channels of the first static mixer allow for passage of a sphere (solid sphere and/or passage without deformation) that is larger than the maximum sphere that can pass (without deformation) through the channels of the second static mixer without touching contact with said mixer. For instance the channels of the second static mixer do not allow for passage for spheres having a diameter equal to or larger than a certain limit diameter and the channels of the first allow for passage of such spheres having that limit diameter. This is further illustrated in FIG. 2 below.

The first static mixer includes at least a first mixing element, e.g. a first baffle, disposed across a ballistic trajectory (a direct path) from each of the inlets in the first section of the shell along a longitudinal direction within the shell towards the second section. The first mixing element provides an impingement surface that extends laterally across the direct path and towards an aperture. The impingement surface is typically not perforated and deflects the first and second fluid laterally, i.e. radially, to the aperture. The distance in the lateral direction between the direct path and the aperture is for example at least 10% or at least 20% of the diameter of the shell and/or at least 20 cm.

The aperture defines a flow channel, for allowing the flow to pass around the first mixing element. Preferably, the first mixing element is the mixing element that is the nearest to the inlets.

The first mixing element comprises for instance a plate, baffle, that extends perpendicular (horizontal in case of a vertically oriented reactor) to an overall flow direction in the shell.

Thus, in use, the first mixing element can advantageously induce a first, initial, mixing of the feeds from the respective inlets by impinging the feeds and diverting the resulting mixture in a lateral direction.

In a strongly preferred embodiment the first static mixer includes a second mixing element, e.g. a second baffle, disposed downstream of the first mixing element. The second mixing element is disposed across a ballistic trajectory, a direct path, between the aperture of the first element and the second section of the shell. The second element provides a second impingement surface that extends laterally across the direct flow path towards a second aperture for allowing the flow to pass the second mixing element. The second impingement surface is preferably not perforated and preferably deflects the fluid laterally, i.e. radially to the aperture. The distance in the lateral direction between the direct flow path and the second aperture is for example at least 10% or at least 20% of the diameter of the shell and/or at least 20 cm.

Figure 2:
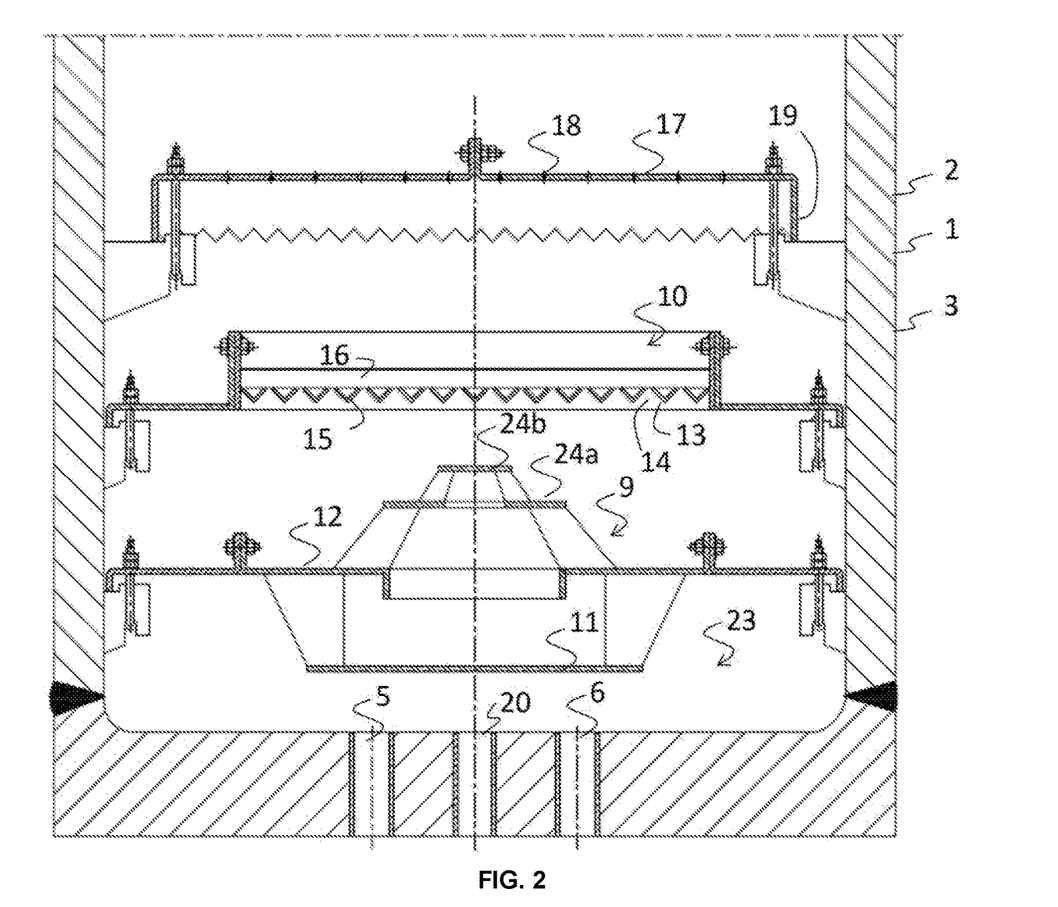
FIG. 2 schematically illustrates a bottom section of an example reactor according to the invention.

The second mixing element comprises for instance a plate, baffle, that extends perpendicular (horizontal in case of a vertically oriented reactor) to an overall flow direction in the shell. The second mixing element, e.g. baffle, preferably overlaps a projection of the first aperture, e.g. as shown in FIG. 2. The second element can advantageously divert the pre-mixed flow along lateral direction toward the second aperture.

Thus, in use, the second element can advantageously induce a second, further, mixing of the reactor contents by impinging the feeds and diverting the mixture in a lateral direction The combination of first and second mixing elements advantageously provides a flow trajectory, e.g. a meandering flow path, along which reactor feeds are mixed. The flow in particular meanders radially, i.e. in a direction perpendicular to the length direction of the reactor.

Accordingly, the first mixer can be understood as a plug flow type mixer directing the reactor content along a meandering pathway for a first initial, coarse, mixing stage.

Preferably, the first mixing element and/or the second mixing element, e.g. plates, is without perforations so as to divert all of the flow along the meandering pathway and to prevent portions of the feed from bypassing the mixing flow path.

In some embodiments of the chemical reactor, the first static mixer comprises a first mixing element that is arranged in the projection from said inlets in the flow direction of fluid from said inlets and that is configured for laterally diverging the flow of the fluid streams, i.e. diverging the flow to a direction perpendicular to said flow direction or length direction, by impingement of said fluid streams on a surface of said first mixing element. The diverging of the flow and the impingement of the fluid provides for a first coarse mixing.

Preferably the first static mixer comprises a first mixing element that is arranged above the first and second inlet, and the reactor is a vertical reactor wherein said first section is a bottom section. Preferably the first mixing element is configured for diverging the flow of the fluid streams in the horizontal direction. For instance, the first mixing element is configured for diverging the fluid flow by impingement of said fluid streams on a substantially horizontal (or horizontal) surface of that mixing element. Preferably the first mixing element is the mixing element that is the nearest to the inlets. Preferably the first and second inlet are each independently configured for supplying a fluid stream in substantially vertical direction into the reactor.

The first mixing element comprises for instance a plate, preferably a plate without perforations wherein the plate is preferably arranged horizontally. In some embodiments the reactor comprises an annular opening between the plate and the shell for fluids. The plate is for instance a disc plate.

For example the reactor is a vertical reactor, wherein the first section is a bottom section and the first static mixer comprises a first mixing element that is arranged above said inlets and configured for diverging the flow of the fluid streams in the horizontal direction by impingement of said fluid streams on a substantially horizontal surface of said first mixing element.

Preferably the first static mixer comprises a disc element and a donut element. Preferably the disc element and the donut element are each arranged horizontally. Preferably these elements are arranged above each other and vertically spaced from each other such that fluid can flow horizontally between these elements. Preferably the disc element completely overlaps the hole of a neighbouring donut element in vertical projection. For example a disc element is arranged between a donut element and the first and second inlet. Preferably the disc element is not perforated. In some embodiments the donut element comprises only one hole for fluid passage. Preferably the first static mixer comprises two pairs of disc-and-donut elements. In an example embodiment the first static mixer comprises, in the general flow direction (e.g. on a line from inlet to outlet) a stack of, in order, a first disc element, a first and a second donut element, the second donut element having a hole (aperture) with a smaller diameter than the hole of the first donut element, and a second disc element. Preferably the second disc element is arranged at least in part in the projection, along the length of the reactor in downstream direction, of an aperture of the second donut element, thereby obstructing flow of fluid passing through said aperture of said second donut element. Preferably the second donut element is arranged, at least in part, in the projection along the length of the reactor in downstream direction, of an aperture of the first donut element, thereby obstructing flow of fluid passing through said aperture of said first donut element. Preferably the first disc element is arranged, at least in part, in the projection of the first and second inlet to the aperture of the first donut element, thereby obstructing direct flow from said first and second inlet to said aperture.

The reactor also comprises a second static mixer positioned downstream of the first static mixer. In contrast to the first mixer the second static mixer comprises one or more elements, e.g. a mesh, perforated plate, or laterally separated bars, configured to diverge, split, the reaction mixture over a plurality of adjacent flow passages. As such the second static mixer can be understood as a mixer, a structured mixer, providing a plurality of adjacent fluid passages, preferably at least 10 or at least 20 flow channels in parallel. The fluid passages are provided in parallel, in particular in parallel in the cross section of the reactor perpendicular to the length of the reactor.

Preferably the adjacent flow channels are narrow and/or provide for a constriction of the lateral cross sectional area of flow by at least 50% or by at least 90%. Downstream of the constriction the fluid expands and turbulence may contribute to good and intimate mixing.

Accordingly, in a preferred embodiment, the second static mixer comprises one or more elements, flow diverging elements, configured to diverge, split, the reactor flow over a plurality of adjacent flow channels.

The characteristic dimension of fluid passages comprised in the second static mixer ($d2$), is smaller than a characteristic dimension of the flow channel ($d1$) comprised in the first static mixer, with the characteristic dimension of the fluid passages respectively flow channels defined by a maximum dimension of a solid sphere that can pass without deformation. Note that for circular passages the characteristic dimension would correspond to the diameter, whereas for square or rectangular passages, e.g. slits, the characteristic dimension would correspond to a separation between opposing edges.

Diverging the coarsely pre-mixed flow from the first static mixer, at the second static mixer, into a plurality of fluid passages having a comparatively smaller characteristic dimension improves contact, e.g. increased interfacial area, between constituents comprised in the respective feeds. For example, flowing a coarsely mixed multiphase fluid flow through passages with increasingly smaller characteristic diameter can reduce dimension of phases within the mix, e.g. gas bubble dimension in a continuous liquid and/or supercritical phase, or a dimension of supercritical phase in a liquid phase. The smaller the characteristic dimension the more intimate the contact between the respective phases. In a preferred embodiment, the characteristic dimension of passages ($d2$) in the second static mixer is at least two times smaller than the characteristic dimension of channels ($d1$) comprised in the first static mixer ($d1/d2 \geq 2$). Preferably, $d1/d2 \geq 4$, more preferably $d1/d2 \geq 10$. More preferably $d1/d2 \geq 20$, e.g. in a range of 20-100.

Accordingly, in another or further preferred embodiment, the plurality of fluid passages have a characteristic dimension ($d2$) as defined by a maximum dimension of a solid sphere that can pass without deformation that is at least 4 times smaller, preferably at least 10 times smaller, most preferably at least 20 smaller, than a characteristic dimension ($d1$) of channels comprised in the first static mixer.

As compared to the characteristic dimension of the reactor D, e.g. diameter, the characteristic mixing parameter Mc for the first static mixer $M_{c,1}$ as defined by $D/d1$ is typically between 1 and 50, preferably between 1-10. The characteristic mixing parameter Mc for the second static mixer ($M_{c,2}$) as defined by $D/d2$ is typically between 10-1000, preferably 50-1000. In addition, $M_{c,2}$ will be larger than $M_{c,1}$ by a factor of at least 2. Preferably $M_{c,2}/M_{c,1} \geq 10$, more preferably $\geq 20$.

Preferably the second static mixer comprises mixing elements, flow diverging elements, which each comprise a (bottom) edge that is adapted for dividing a flow of the fluid reaction medium in the reactor into two sub-flows. Preferably the second static mixer further comprises channels for said sub-flows. Preferably the channels are tapered and converging in the flow direction, e.g. in upward direction for a vertical reactor with inlets at the bottom. The converging channels provide a constriction (choking) that increases a velocity of the sub-flows, forming a plurality of downstream fluid jets of upon exiting the channels. This may contribute to thorough mixing. The tapering of the converging channels advantageously provides for a relatively low pressure drop over the mixing element. In some embodiments, the second static mixer comprises one or a plurality of horizontal layers of said mixing elements, wherein adjacent mixing elements in such a layer are spaced apart from each other horizontally to allow for passage of fluids. In some embodiments, the second static mixer comprises at least two of such horizontal layers of mixing elements, wherein the layers are vertically stacked.

Preferably the second static mixer comprises one or more layers of parallel angle bars, each angle bar comprising side edges. The angle bars preferably point to the first and second inlet. The side edges of adjacent angle bars are spaced apart from each other to allow for passage of fluid through openings between the angle bars.

It will be understood that tapered channels can also be provided by a number of alternative means, including but not limited to tapered perforations, e.g. in a plate and a mesh with tapered sidewalls.

Preferably the second static mixer comprises at least two of said layers of angle bars, wherein said layers are vertically stacked. For instance, the angle bars in vertically adjacent layers are arranged at an angle to each other in the horizontal plane. For example angle bars in vertically adjacent layers are arranged at 30°-90°, e.g. at 90°, to each other in the horizontal plane. For instance the angle bars in two vertical adjacent layers cross each other in vertical projection in crossing points in the horizontal plane. For instance the angle bars of two vertically adjacent layers are in touching contact at these crossing points. For instance bottom edges of angle bars of an upper layer are in touching contact with upper side edges of a lower layer of mixing elements.

Preferably, the fluid passages as comprised in the second static mixer are disposed along a central position of the shell whereas an outer perimeter, around the passages is configured to disallow fluid passage and direct an incoming flow along the sidewalls of the shell toward the central portion. The second portion can for example be provided by a plate, e.g. a donut shaped plate, preferably a non-perforated plate.

Advantageously, the mixing elements, e.g. first and or second layers of bars, can be mounted, fixed, to the plate, that can be affixed to the shell walls as a single unit, mitigating down time during service.

Accordingly, in a preferred embodiment the second static mixer comprises a first portion with the one or more mixing elements, e.g. angle bars, and a second portion, e.g. a plate, configured to divert flow to the central position.

Figure 2A:
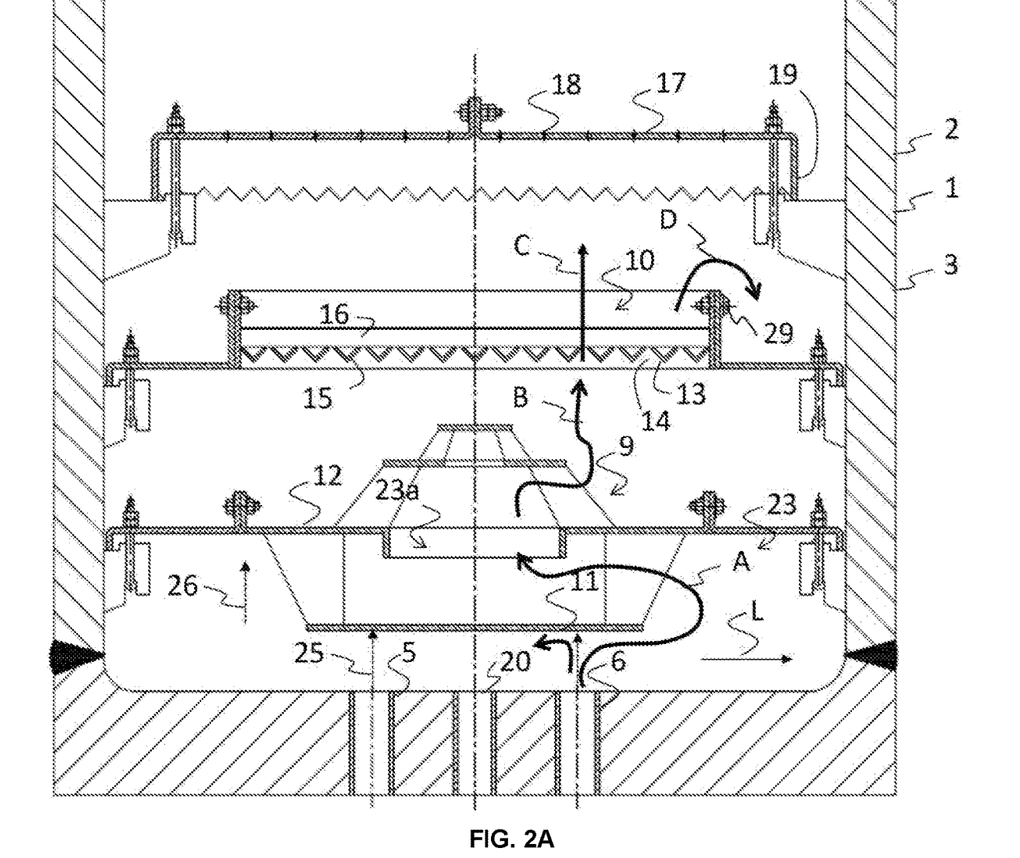
FIG. 2A schematically illustrates additional details of the bottom section.

In yet further preferred embodiments, particularly for vertically configured reactors, the second static mixer comprises an overflow barrier. The overflow barrier can be provided to the second portion, e.g. as shown in FIG. 2A. Preferably, the overflow barrier forms a rim along a boundary between the first and second portions, e.g. a rim circumferentially provided along an inner perimeter of a donut-shaped plate. The overflow barrier can be used to mount the mixing elements, e.g. the first and/or further layers of angle bars. Inventors found that providing the overflow barrier, rim, can further contribute to more intimate mixing of reaction mixture constituents, in particular, for reactions comprising one or more gas or supercritical phases and a liquid phase.

Without wishing to be bound by theory inventors find that passing the reaction mixture through a second mixing element comprising an overflow edge can preferentially guide lower density phase(s) of the mix along a middle (central) portion of the reactor, whereas higher density phase(s) are directed towards the cylindrical shell. Preferentially guiding higher density phases towards the shell wall can advantageously increase mixing of fluids as the higher density phase is spread over a larger surface, giving an improved contact and/or heat exchange with the lower density phase.

The reactor for instance further comprises a gas distributor arranged in the first section of the shell downstream of the second static mixer. The reactor is for instance a vertical reactor wherein the first section is a bottom section. In such embodiment, the gas distributor comprises for example a horizontal perforated plate. In some embodiments, the horizontal perforated plate is provided with a downward rimmed edge and the reactor comprises an annular space between the perforated place and the internal wall of the reactor for fluid flow. In operation a gas cushion may form under the gas distributor. Preferably the vertical distance between the bottom of the gas distributor and the top of the second static mixer is less than 5% of the length of the reactor. The gas distributor can for instance be used in embodiments wherein the reactor is a urea synthesis reactor.

FIG. 2 schematically illustrates a first section, being a bottom section, of an example reactor according to the invention with a first and a second static mixer. References 1-10 are the same as for FIG. 1. The fluid flow is illustrated in FIG. 2A.

The first static mixer (9) comprises disc element (11) and donut element (12) both horizontally arranged and vertically spaced apart from each other. The disc element is arranged in the projection of the first and second inlet and obstructs the fluid flow from the first and second inlet, deflecting the fluid in lateral direction, radially outward, to the annular opening (23) between the disc element (11) and the shell (2). The donut element (12) in turn obstructs straight flow from the opening (23) and deflects the flow radially inward. The fluid meanders around the disc element and between the disc and donut element (flow line A). Downstream of the donut element aperture a second meandering flow (B) is provided by the downstream donut element (24a) and disc element (24b).

Thereby the first static mixer comprises a first baffle (11) disposed across a ballistic trajectory (25) from the first inlet (5) towards the second section and also across the ballistic trajectory from the second inlet (6) the towards the second section. The first baffle provides a first impingement surface for said first fluid and said second fluid (namely the bottom surface), wherein the impingement surface extends laterally (L) towards the aperture (23).

The first static mixer thereby also comprises at least a second baffle (12) disposed across a ballistic trajectory (26) between the aperture (23) of the first element and the second section, said second baffle providing a second impingement surface that extends laterally, e.g. radially inwards, towards a second aperture (23a) for allowing the reaction mixture to pass the second mixing element, wherein the second baffle overlaps a projection of the first aperture, to provide for a meandering flow path (A, B) for the fluid through the first static mixer The reactor as illustrated comprises an optional third inlet (20) in the first section for a third fluid stream.

The second static mixer (10) comprises mixing elements which each comprise an edge (13) that is adapted for dividing a flow of the reaction medium in the reactor into two sub-flows (C2). The second static mixer further comprises channels (14) for said sub-flows (C1, C2). The channels are tapered and converging in the upward direction. The channels (14) are arranged in parallel in the cross-section perpendicular to the length of the reactor, e.g. are provided as parallel channels in a horizontal cross-section. The downstream, most converged part (27) of the channels (14) is very narrow, providing significant constriction and expansion and turbulence in the zone (28) immediately downstream of the narrow end of the channels (see FIG. 3.).

The second static mixer (10) comprises two stacked layers (15, 16) of angle bars. The angle bars are at an angle of 90° between the two layers in the illustrated example, crossing angles in the range of e.g. 30° to 90° can for example be used. The angle bars in adjacent layers are for instance in touching contact with each other.

The opening in the donut element (12) and the spacing between the disc element (11) and donut element (12) allows for passage of spheres without deformation, e.g. without touching contact with said elements, through the first static mixer, for spheres up to a certain maximum size. Spheres with this maximum size can not pass through the narrow channels (14) of the second static mixer. The second static mixer is accordingly configured for more intimate mixing of fluids than the first static mixer. As illustrated, the first static mixer uses radial deflection and the second static mixer in particular uses in particular converging channel to induce turbulence and intimate mixing. The combination of two different types of static mixing was found to provide for good mixing especially for urea synthesis reactor feed streams. The two types of static mixing do not depend on gravity and can be used also e.g. in a horizontal reactor.

At the downstream side of the second static mixer, an overflow barrier (29) is provided which contributes to distribution of in particular higher density phase, illustrated with flow line (D).

The example bottom section as illustrated further comprising an optional gas distributor (17) arranged above the second static mixer (10). The gas distributor comprises a horizontal perforated plate (18) with a downward rimmed edge (19). In operation a cushion of low density fluid fraction (gas cushion) is formed underneath the perforated plate and the high density fluid fraction, e.g. the liquid, such as formed urea and water, flows around the perforated plate through the annular space between the rim (19) and the shell (2) whereas the lower density fluid fraction, e.g. the gaseous and/or supercritical components, flow through the perforations in the plate (18). In this way bubbles of lower density fluid components, e.g. bubbles of the gaseous and/or supercritical components are redistributed.

In an example embodiment, the reactor of FIG. 2 is a urea synthesis reactor having at the bottom three separate inlets for $NH_3$ feed, $CO_2$ feed, and carbamate recycle, respectively.

Figure 3:
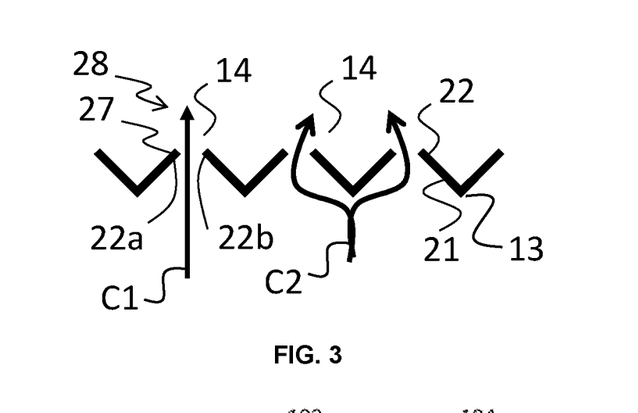
FIG. 3 schematically illustrates details of an example second static mixer used in the invention.

FIG. 3 schematically illustrates details of an example mixing element of a second static mixer used in the invention. The second static mixer comprises a horizontal layer of parallel downward pointing angle bars (21) comprising side edges (22). The side edges (22a, 22b) of adjacent angle bars are spaced apart from each other to allow for fluid flow (C1, C2) through openings (14) between the angle bars. The side edges provide for tapered converging channels (14) with the angle bars essentially providing an obstructing surface and with the space between the side edges defining the flow area through a lateral cross section through the mixing element. It can be seen that the adjacent flow channels (14) provide for a constriction of the lateral (horizontal in the figure) cross sectional area of flow by at least 50%.

In a preferred embodiment of the reactor, the mixing elements of the first and second static mixer are each made of duplex ferritic-austenitic stainless steel. This is particularly preferred for embodiments wherein the chemical reactor is a urea synthesis reactor. The shell of the reactor may also comprise an internal lining made of duplex ferritic-austenitic stainless steel.

For example ferritic-austenitic duplex stainless steel is used having a Cr content of between 26 and 35 wt. % and Ni content of between 3 and 10 wt. %.

For instance the elementary composition of the duplex ferritic-austenitic stainless steel comprises or consists of, in percentages by weight: C 0-0.05; Si 0-0.8; Mn 0-4.0; Cr 26-35; Ni 3.0-10; Mo 0-4.0; N 0.30-0.55; Cu 0-1.0; W 0-3.0; S 0-0.03; Ce 0-0.2; the balance being Fe and unavoidable impurities.

In an embodiment, the elementary composition of the duplex ferritic-austenitic stainless steel comprises or consists of, in percentages by weight: C 0-0.030; Mn 0.8-1.50; S 0-0.03; Si 0-0.50; Cr more than 29-30.0; Ni 5.8-7.5; Mo 1.50-2.60; W 0-3.0; Cu 0-0.80; N 0.30-0.40; Ce 0-0.2; the balance Fe and unavoidable impurities. In a further embodiment the elementary composition of the duplex ferritic-austenitic stainless steel comprises or consists of, in percentages by weight: C 0-0.03; Si 0-0.5; Mn 0.3-1; Cr more than 29-33; Ni 3-10; Mo 1.0-1.3; N 0.36-0.55; Cu 0-0.8; W 0-2.0; S 0-0.03; Ce 0-0.2; the remainder being Fe and unavoidable impurities.

The duplex ferritic-austenitic stainless steel alloys can also be referred to as iron-based alloys. Optionally the duplex ferritic-austenitic stainless steel alloys contain a non-zero amount of C.

Suitable duplex stainless steel alloys include for example the steel available as Safurex® steel and having composition 29Cr-6.5Ni-2Mo—N, which is also designated by ASME Code 2295-3 and by UNS S32906, and steel available as DP28W™ steel and having composition 27Cr-7.6Ni-1Mo-2.3W—N, which is also designated by ASME Code 2496-1 and by UNS S32808.

Other duplex ferritic-austenitic stainless steel alloys may also be used. Other corrosion resistant steel alloys and other corrosion resistant materials may also be used. Finally, other construction materials may also be used for the first and second static mixer, for instance if the chemical reactor is used for compounds which are not corrosive.

The preferred mixing of $CO_2$ and ammonia under formation of ammonium carbamate in the preferred urea synthesis reactor is strongly exothermic and may lead to hot spots and subsequent corrosion of the reactor. The above-mentioned duplex stainless steel alloys in combination with the herein described construction of the first and second static mixer advantageously address this corrosion risk for the mixing zone. In particular crevice corrosion may be avoided with the first and second static mixer according to the present invention. Additionally the preferably used gas distributor is optionally also made of duplex ferritic-austenitic stainless steel, preferably a duplex steel alloy as discussed herein.

An aspect of the invention pertains to a mixing process carried out in a chemical reactor according to the invention, wherein at least a first and a second fluid are mixed in the mixing zone, preferably at a pressure above 100 bar, and optionally are further mixed with at least additional fluid from e.g. a third inlet for fluid.

The first and second fluid have a different chemical composition. In some embodiments, the first fluid stream is a liquid at the first inlet and the second fluid stream is a gas at the second inlet.

A further aspect of the invention pertains to a method of reacting, combing, and/or mixing a first and a second chemical compound, wherein the method comprises: supplying said first fluid stream comprising said first compound and said second fluid stream comprising said second compound to the chemical reactor according to the invention and bringing said first and second compound in contact with each other in said mixing zone of the chemical reactor, and preferably mixing said first and second compound in said mixing zone using said first and second static mixer and preferably allowing the first and second compound to react with each other. The chemical reactor is for instance operated at a pressure above 100 bar.

In these methods and in the urea production process of the invention, the method preferably comprises mixing the fluids in the reaction mixture in both the first and the second static mixer wherein the fluids are mixed more intimately in the second mixer than the first static mixer.

The inventive chemical reactor is for instance a urea synthesis reactor.

The invention also pertains to a urea production plant comprising such a urea synthesis reactor. The invention also pertains to a urea production process carried out using such a urea synthesis reactor and/or carried out in such a urea production plant.

In a urea production process as described herein, the first fluid stream for instance has a higher wt. % of $NH_3$ than the second fluid stream. In some example embodiments, the first fluid stream is the $NH_3$ feed. In some example embodiments, the second fluid stream is the $CO_2$ feed.

The first fluid stream comprises in some embodiments for instance also carbamate solution. The carbamate solution is for instance supplied from a HP carbamate condensation unit or from a recovery section. In some embodiments the urea plant comprises an ejector, driven by $NH_3$ feed, and having an inlet for carbamate recycle solution to be transported and having an outlet connected to an inlet, e.g. said first inlet, of the inventive urea synthesis reactor.

In some embodiments, the urea synthesis reactor comprises a separate third inlet in said bottom section for carbamate recycle solution.

Because the intermediate compound ammonium carbamate is extremely corrosive at urea synthesis conditions, it is important for urea synthesis reactors that the parts in contact with reaction medium are corrosion resistant. For instance, the inner surface of the shell is made of corrosion-resistant materials, for example duplex stainless steel. Moreover, since the carbamate formation reaction is exothermic and fast, there is a risk of hot spots in the mixing zone. The formed ammonium carbamate can be even more corrosive in such hot spots.

The reactor comprises for instance a shell (e.g. of carbon steel) and an internal layer of a corrosion resistant material, for instance an internal lining or overlay weld of a corrosion resistant material. The corrosion resistant material is e.g. a duplex stainless steel. The example elemental steel compositions described hereinbefore for duplex stainless steel may also be used, for example, for such internal layer of the reactor. Such internal layer is for instance used typically for urea reactors.

The urea synthesis reactor is for instance a vertical cylindrical reactor with the first and second inlet at the bottom. In this embodiment, the urea synthesis reactor comprises for instance a plurality of vertically spaced, horizontally disposed perforated reactor trays which are arranged above the second static mixer.

An aspect of the invention pertains to urea production plant comprising a high pressure synthesis section comprising an inlet for $NH_3$ feed, an inlet for $CO_2$ feed, and a chemical reactor according to the invention as urea synthesis reactor. The chemical reactor comprises the mixing zone with the first and second static mixer as discussed. The inlet for $CO_2$ feed is typically connected to a HP $CO_2$ compressor and the inlet for $NH_3$ feed is connected typically to a HP ammonia pump.

The reactor comprises an outlet for urea synthesis stream which is connected to a carbamate dissociation section. One or more carbamate dissociation sections may be used. The carbamate dissociation section comprises a heat exchanger and/or an expansion valve. Typically the carbamate dissociation section comprises a heat exchanger for heating the urea synthesis stream. Preferably the carbamate dissociation section comprises a vertical falling-film shell-and-tube heat exchanger configured for receiving urea solution at the upper inlet of the tubes. For instance the heat exchanger is a high pressure stripper.

The plant may comprise one or more urea synthesis reactors, in parallel and/or in series. One or more of the urea synthesis reactors may be a chemical reactor according to the invention with a mixing zone as described herein.

The inventive urea synthesis reactor may be used for a urea production process which comprises reacting $NH_3$-containing feed and $CO_2$-containing feed to form ammonium carbamate and dehydration of ammonium carbamate to urea and water under urea-forming conditions in a urea synthesis reactor, wherein the urea synthesis reactor is a chemical reactor according to the invention comprising the mixing zone. The urea synthesis reactor is a vertical reactor with the first and second inlet at the bottom. The urea synthesis reactor for instance serves as an autoclave.

The reactor overall approaches a plug-flow configuration so that at the bottom predominantly feed is present. The carbamate condensation reaction is fast and highly corrosive ammonium carbamate is formed in a bottom zone of the reactor.

Preferably the reactor is operated at a pressure above 100 bar, e.g. in the range of 100-350 bar. For instance, the reactor is operated at a temperature above 125° C., e.g. above 140° C., such as in the range 125-250° C. or 140° C.-250° C., e.g. in the range 180-230° C. For instance the density of the $NH_3$-containing feed is more than 100 kg/m³ and the density of the $CO_2$-containing feed at the reactor inlet is more than 100 kg/m³.

In the process, the urea synthesis stream is withdrawn from an upper part of the reactor, optionally using a downcomer and optionally in combination with gas/liquid separation. Optionally the reactor has only one outlet for effluent, optionally the reactor comprises an outlet for a gaseous stream (so-called 'inerts') and an outlet for a urea synthesis solution.

In some embodiments, the urea synthesis reactor of the urea plant and process is fed with an essentially gaseous stream of carbon dioxide and an essentially liquid stream of ammonia or ammonia/ammonium carbamate, wherein the term 'essentially gaseous' and 'essentially liquid' also includes supercritical. In some embodiments, the $NH_3$ feed stream has a higher gravimetric density than the $CO_2$ feed stream.

Typically, reagents (e.g. $CO_2$ feed and $NH_3$ feed) are fed into the reactor from below, through a bottom part of the reactor. A uniform distribution of the reagents over the horizontal cross-section of the urea reactor is to be achieved, desirably in a bottom part of the reactor occupying desirably a small part of the reactor length. Achieving good mixing of fluid feed components over a small part of the reactor length contributes to optimum use of the reactor volume. However, achieving such mixing is challenging.

The urea synthesis reactor according to the present invention addresses this problem of achieving good mixing of the feed components of a urea synthesis reactor at least in part by using the mixing zone with the first and second static mixer as described herein.

The urea production process comprises purification of the urea synthesis stream in one or more dissociation sections, typically by expanding the high pressure urea synthesis stream to lower pressure than synthesis pressure and/or heating, and gas/liquid separation to give urea solution and a gas stream. The components of the gas stream ($CO_2$ and $NH_3$ gas) are preferably at least in part recycled to the urea synthesis section after condensation.

The urea solution after sufficient purification is for instance subjected to a concentration step, such as in one or more vacuum evaporators, to give a urea melt. The urea melt is for instance subjected to solidification in a finishing section.

The finishing section is for instance a granulator or a prilling tower or another type of finishing section. The urea melt may also be used at least in part e.g. for melamine production. The purified urea solution may also be used at least in part as liquid stream, e.g. for producing liquid fertilizer. The urea product can be used e.g. as fertilizer or e.g. as Diesel Exhaust Fluid or e.g. as feed for a melamine plant.

The urea synthesis reactor according to the invention can be used in many types of urea production processes, including for example stripping-type processes, total recycle processes and even once-through processes. The urea synthesis reactor can be used in urea production processes wherein at least two separate fluid streams are provided to the reactor, particularly wherein at least two separate fluid streams are provided to the bottom of a vertical urea synthesis reactor.

In some embodiments, the urea production process is of the so-called 'once-through' type. In such an embodiment, the urea reactor receives $CO_2$ feed and $NH_3$ feed to give a urea synthesis stream. The reactor does not receive any recycle stream from recovery of components from the urea synthesis stream. In a typical embodiment with a urea plant of the once-through type, $CO_2$-feed and $NH_3$-feed are supplied into the bottom of the reactor, which is a vertical vessel, and reactor effluent is withdrawn at the top of the reactor.

In some embodiments, the urea production process involves recycle of at least part of at least one component from the urea synthesis stream to the high pressure synthesis section. Typically, the reactor effluent is subjected to expansion to a lower pressure than synthesis pressure and/or heating, in one or more stages, and gas/liquid separation, to give urea solution and off-gas. The off-gas typically comprises $CO_2$ and $NH_3$, which are at least in part and typically after condensation recycled to the high pressure urea synthesis section. In some embodiments at least part of the off-gas is condensed into carbamate solution and optionally liquid $NH_3$ and the carbamate solution and optionally liquid $NH_3$ is recycled at least in part to the high pressure synthesis session.

In some embodiments, the plant is of the total recycle type and the process includes recycle of carbamate solution, obtained by condensation of a gas stream comprising $CO_2$ and $NH_3$, which gas stream is obtained from purification of the reactor effluent by a carbamate dissociation step, which is carried out at e.g. at high pressure, medium pressure, or low pressure.

In a particular embodiment, the urea production plant comprises a high pressure stripper, wherein in the process the reactor effluent is subjected to stripping at high pressure, using counter-current contacting with a strip gas and heating. The strip gas is e.g. $CO_2$ feed, $NH_3$ feed, or is obtained by heating the urea solution (self-stripping or thermal stripping). The stripper is for instance a falling-film shell-and-tube heat exchanger with urea solution in the tubes. The stripper has an outlet for a mixed gas stream comprising $CO_2$ and $NH_3$ and an outlet for stripped urea solution. In embodiments with a urea plant and process of the stripping type, the HP urea synthesis section is operated e.g. at 120-180 bara.

In some embodiments, at least a part of the mixed gas stream is supplied to a high pressure carbamate condenser, which is e.g. a horizontal or vertical condenser and which is e.g. a submerged condenser. The high pressure carbamate condenser is for instance a shell-and-tube heat exchanger with the gas to be condensed e.g. in the tubes or in the shell. In such a HP carbamate condenser, at least part of the gas from the HP stripper is at least partly condensed into ammonium carbamate comprised in a liquid stream. This liquid stream can be referred to as carbamate solution.

In some embodiments, a part of the gas from the stripper is supplied directly to the urea synthesis reactor, wherein the urea synthesis reactor receives gas from the stripper at an inlet at a bottom of the reactor. In some embodiments, the urea synthesis reactor comprises two inlets at the bottom of the reactor, one for carbamate solution and one for a mixed gas stream from the stripper.

The urea synthesis reactor may for instance also be a pre-reactor as described in US 2015/0322000A1. The reactor may for instance receive carbamate solution from a recovery section and a part of the gas stream from a high pressure stripper.

The urea reactor design of the present invention is for example, without restriction, useful in embodiments wherein a high pressure stripper is used of the 'self-stripping type'. In such plants, the $NH_3$ feed is typically introduced into the urea reactor. An example is the so-called 'Snamprogetti' type urea production process.

In some embodiments, the urea production process is of the type with a high pressure stripper using $CO_2$ as strip gas. In some embodiments a first part of the $CO_2$ feed is supplied to the stripper and a second part of the $CO_2$ feed is supplied as gaseous feed stream to the reactor. Additionally in some embodiments $NH_3$ feed is supplied to the reactor, optionally in a mixture with carbamate. Typically, the reactor has two or more inlets at the bottom of the reactor. In such a urea production process, the urea reactor design of the present invention can be used with good results. An example of such a process is the 'Avancore' process with a pool condenser as illustrated in Ullmann's Urea, 2010, FIG. 22.

Yet another example is a process using an after-reactor, for example a process as described in FIG. 1 of US 2015/0119603.

Another example is the ACES21 process as illustrated in Ullmann's Urea, 2010, FIG. 28.

The design of the reactor may for instance also be used in embodiments where the plant comprises a HP $CO_2$ stripper, $NH_3$ feed is supplied to the reactor, and gas and liquid from one or more HP carbamate condensers are also supplied to the reactor, separately from the $NH_3$ feed. An example is the ACES process illustrated in Ullmann's Urea, 2010, FIG. 27.

In other embodiments, a part of the gas stream from the HP stripper using $CO_2$ feed as strip gas is supplied to a urea synthesis reactor which is a chemical reactor having a mixing zone according to the invention.

In embodiments wherein the urea production plant and process are of the type with a HP $CO_2$ stripper, and also in other embodiments of the urea production plant and process, the plant may comprise two or even more urea synthesis reactors, wherein for instance at least one reactor is a chemical reactor with a mixing zone as described herein.

In some embodiments, the urea production process described herein involves recycle of carbamate solution from a recovery section to the urea synthesis section, without a high pressure stripper. In such embodiments, the HP urea reactor is operated e.g. at a pressure of 180-250 bara. The reactor is for instance operated at a pressure higher than 190° C. and at a pressure of 180-250 bar. These pressures and temperatures are higher than typically used for urea plants with high pressure strippers. Especially at these higher temperatures there is an increased risk of corrosion by the ammonium carbamate present in the reactor.

An example of such a process is illustrated in Ullmann's Urea, 2010, FIG. 12, except that in the illustrated process an external mixer is used for mixing the $CO_2$ feed, the $NH_3$ feed and the carbamate recycle stream. In the present invention, the mixing zone is internal to the reactor. Thereby the invention advantageously provides for improved mixing, less corrosion risks, and simpler design with fewer pieces of high pressure equipment. The static mixers used in the present invention advantageously have a simple and robust design.

In some embodiments, the reactor effluent (urea synthesis stream) from the HP urea reactor is expanded to medium pressure (MP) and subjected to dissociation with heating at MP to give MP off-gas and an MP urea solution, the MP off-gas is condensed in an MP carbamate condenser to give an MP carbamate solution and condensed in an ammonia condenser to give an ammonia recycle stream. The MP carbamate condenser and the ammonia condenser may operate at different temperatures and/or pressures. The MP carbamate solution is pumped back to the HP urea reactor and the ammonia recycle stream is also pumped back to the HP urea reactor. The MP urea solution is further expanded to low pressure (LP) and subjected to LP dissociation with heating, to give purified LP urea solution and LP off-gas. The LP off-gas is condensed in an LP carbamate condenser to give LP carbamate solution which is also recycled to the HP urea reactor, typically through the MP section.

Figure 4:
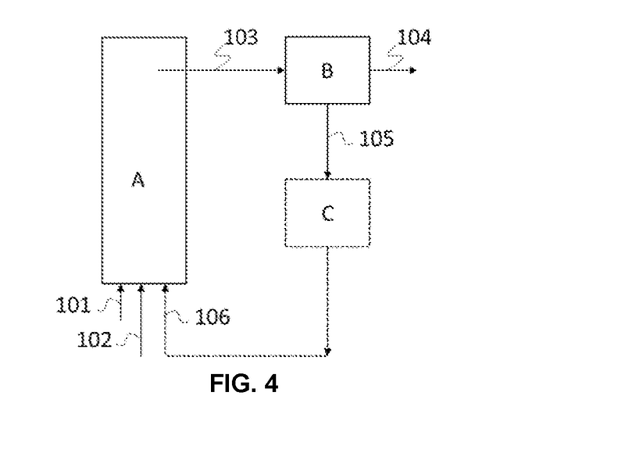
FIG. 4 schematically illustrates an example process scheme of a urea production process according to the invention.

FIG. 4 schematically illustrates an example process scheme of a urea production process according to the invention. $CO_2$ feed (101) and $NH_3$ feed (102) are supplied to the high pressure reactor (A). The high pressure reactor (A) is a chemical reactor according to the invention with a first and a second static mixer, in particular a urea synthesis reactor according to the invention. The reactor effluent (103) comprises urea, water, ammonium carbamate and water and is purified, optionally after expansion of the reactor effluent from high pressure to e.g. medium pressure, in a dissociation section (B) which includes a gas/liquid separation step to give purified urea solution (104) and off-gas (105). The off-gas is optionally condensed in an optional condenser (C) and optionally recycled as carbamate solution (106) to the reactor. The dissociation section (B) comprises for instance a high pressure stripper or for instance a medium pressure decomposer and for instance involves heating of the reactor effluent to promote the dissociation of ammonium carbamate.

In a preferred embodiment of the urea production process and urea plant of FIG. 4, the reactor (A) comprises a bottom section as illustrated in FIG. 2. In a preferred embodiment of the illustrated urea production process, the condenser (C) is used. In a particular embodiment, dissociation section (B) comprises a medium pressure decomposer for heating reactor effluent, in particular urea synthesis solution, and the optional condenser (C) is a medium pressure condenser. The plant further comprises a low pressure (LP) recovery section receiving urea solution from the dissociation section (B).

The term 'typically' as used herein indicates features that are frequently used, but are not mandatory.

As used herein, "carbamate" refers to ammonium carbamate.

As used herein, HP (high pressure) indicates a pressure of e.g. at least 100 bara, e.g. 120-250 bara, 110-160 bara, MP (medium pressure) indicates a pressure of e.g. 20-80 bara, and LP (low pressure) indicates a pressure of e.g. 1-10 bara, e.g. 4-10 bara; these pressure ranges are for process solutions and not necessarily the same for steam and heating fluids. The abbreviation "bara" means bar absolute.

As used herein, 'fluid' includes gas, liquid, and super-critical fluids, and mixtures thereof.

As described hereinbefore embodiments of the disclosure pertain to a chemical reactor comprising a mixing zone comprising first static mixer and a second static mixer both arranged in shell of the reactor, wherein the second static mixer is positioned further from said first inlet than said first static mixer, wherein the second static mixer is preferably adapted for more intimate mixing of fluids in the reaction mixture than the first static mixer.

The invention claimed is:

1. A chemical reactor comprising a shell for holding a reaction mixture, a first section and a second section in said shell, a first inlet for a first fluid stream and a second inlet for a second fluid stream, wherein both inlets are arranged in said first section, the reactor further comprising an outlet for reactor effluent withdrawn from said second section, and a mixing zone in said first section of the reactor adapted for mixing said first and second fluid stream,
   wherein the mixing zone comprises a first static mixer and a second static mixer both arranged in said shell, wherein the second static mixer is positioned further from said first inlet than said first static mixer, wherein the second static mixer provides a plurality of adjacent fluid passages that have a characteristic dimension (d2) that is at least 4 times smaller than a characteristic dimension (d1) of channels comprised in the first static mixer, wherein d1 and d2 are respectively defined by a maximum dimension of a solid sphere that can pass without deformation.

2. The chemical reactor according to claim 1, wherein the first static mixer comprises a first baffle disposed across a first ballistic trajectory from each of the inlets towards the second section, said first baffle providing a first impingement surface for said first fluid and said second fluid, wherein the first impingement surface extends laterally towards a first aperture, wherein said first aperture defines a flow channel for allowing the reaction mixture to pass the first baffle.

3. The chemical reactor according to claim 1, wherein the second static mixer comprises one or more mixing elements configured to diverge the reaction mixture over a plurality of adjacent flow channels that provide for a constriction of the lateral cross sectional area of flow by at least 50%.

4. The chemical reactor according to claim 2, wherein the first static mixer comprises at least a second baffle disposed across a second ballistic trajectory between the first aperture and the second section, said second baffle providing a second impingement surface that extends laterally towards a second aperture for allowing the reaction mixture to pass the second mixing element, wherein the second baffle overlaps a projection of the first aperture, to provide for a meandering flow path for the fluid through the first static mixer.

5. The chemical reactor according to claim 1, wherein a characteristic mixing parameter of the first static mixer (Mc,1) is between 1 and 50 and a characteristic mixing parameter of the second static mixer (Mc,2) is between 10 and 1000, wherein Mc,1 and Mc,2 are defined by the diameter of the reactor (D) divided by d1, respectively by d2, and wherein Mc,2/Mc,1≥10.

6. A chemical reactor according to claim 1, wherein the first static mixer comprises a first mixing element that is arranged in the projection from said inlets in the flow direction of fluid from said inlets and that is configured for diverging the flow of the fluid streams to a direction perpendicular to said flow direction by impingement of said fluid streams on a surface of said first mixing element.

7. The chemical reactor according to claim 1, wherein said first static mixer comprises a disc element and a donut element.

8. The chemical reactor according to according to claim 1, wherein the second static mixer comprises mixing elements which each comprise an edge that is adapted for dividing a flow of a reaction medium in the reactor into two sub-flows, the second static mixer further comprising channels for said sub-flows, wherein said channels are tapered and converging in the flow direction.

9. The chemical reactor according to claim 1, wherein said second static mixer comprises one or more layers of parallel angle bars pointing to said inlets and comprising side edges, wherein the side edges of adjacent angle bars are spaced apart from each other to allow for fluid flow through openings between the angle bars.

10. The chemical reactor according to claim 9, wherein said second static mixer comprises at least two of said layers of angle bars, wherein said layers are vertically stacked, wherein the angle bars in vertically adjacent layers are arranged at an angle to each other in the horizontal plane.

11. The chemical reactor according to claim 1, further comprising a gas distributor arranged in said first section of said shell downstream of said second static mixer.

12. The chemical reactor according to claim 1, wherein the first and second static mixer are each made of duplex ferritic-austenitic stainless steel.

13. A urea production plant comprising a high pressure synthesis section comprising an inlet for $NH_3$ feed, an inlet for $CO_2$ feed, and a chemical reactor according to claim 1 as a urea synthesis reactor, wherein said outlet is for a urea synthesis stream and is connected to a carbamate dissociation section comprising a heat exchanger and/or an expansion valve.

14. A urea production process comprising reacting a NH3-containing feed stream and a CO2-containing feed stream to form ammonium carbamate and dehydration of ammonium carbamate to urea and water under urea-forming conditions in a chemical reactor according to claim 1 as a urea synthesis reactor.

15. The urea production process of claim 14, wherein the reactor is operated at a pressure above 100 bar and above 140° C., and wherein the NH3-containing feed and the CO2-containing feed are both introduced into the reactor at a pressure above 100 bar.

16. A mixing process carried out in a chemical reactor according to claim 1, wherein at least said first and said second fluid are mixed in the mixing zone.

17. The chemical reactor according to claim 7, wherein said disc element and said donut element are not perforated.

18. The chemical reactor according to claim 11, wherein the gas distributor comprises a horizontal perforated plate with a downward rimmed edge.

19. The chemical reactor according to claim 11, wherein the vertical distance between said gas distributor and said second static mixer is less than 5% of the length of the reactor.

20. The urea production plant according to claim 13, wherein the carbamate dissociation section comprises a vertical falling-film shell-and-tube heat exchanger configured for receiving urea solution at an upper inlet of the tubes.

21. The mixing process according to claim 16, wherein at least said first and said second fluid are mixed in the mixing zone at a pressure above 100 bar.

22. A chemical reactor comprising a shell for holding a reaction mixture, a first section and a second section in said shell, a first inlet for a first fluid stream and a second inlet for a second fluid stream, wherein both inlets are arranged in said first section, the reactor further comprising an outlet for reactor effluent withdrawn from said second section, and a mixing zone in said first section of the reactor adapted for mixing said first and second fluid stream,
　　wherein the mixing zone comprises a first static mixer and a second static mixer both arranged in said shell, wherein the second static mixer is positioned further from said first inlet than said first static mixer,
　　wherein said first static mixer comprises a disc element and a donut element,
　　wherein the second static mixer comprises mixing elements which each comprise an edge that is adapted for dividing a flow of the reaction medium in the reactor into two sub-flows, the second static mixer further comprising channels for said sub-flows, wherein said channels are tapered and converging in the flow direction.

23. A chemical reactor comprising a shell for holding a reaction mixture, a first section and a second section in said shell, a first inlet for a first fluid stream and a second inlet for a second fluid stream, wherein both inlets are arranged in said first section, the reactor further comprising an outlet for reactor effluent withdrawn from said second section, and a mixing zone in said first section of the reactor adapted for mixing said first and second fluid stream,
　　wherein the mixing zone comprises a first static mixer and a second static mixer both arranged in said shell, wherein the second static mixer is positioned further from said first inlet than said first static mixer,
　　wherein the first static mixer and the second static mixer each comprises mixing elements and channels for reaction mixture to flow through the shell, wherein the channels comprised in the second static mixer are narrower than the channels comprised in the first static mixer, wherein the first section extends over up to 10% of the length of the reactor and comprises the first and second static mixer as well as the first and second inlet;

and wherein the second static mixer is arranged downstream of the first static mixer, relative to the flow of the first and second fluid stream.

\* \* \* \* \*